United States Patent [19]
Chow

[11] Patent Number: 6,161,545
[45] Date of Patent: Dec. 19, 2000

[54] USE OF PULSED ULTRASONICS IN SURGICAL APPLICATIONS

[76] Inventor: James C. Y. Chow, 3001 Caroline St., Mount Vernon, Ill. 62864

[21] Appl. No.: 09/041,072

[22] Filed: Mar. 10, 1998

[51] Int. Cl.$^7$ ................................................. A61B 17/00
[52] U.S. Cl. ............................................................ 128/898
[58] Field of Search ................................ 128/898; 606/1, 606/169; 607/97

[56] References Cited

U.S. PATENT DOCUMENTS

| | | | |
|---|---|---|---|
| 4,192,294 | 3/1980 | Vasilevsky et al. | 606/127 |
| 4,745,920 | 5/1988 | Forssmann et al. | 606/128 |
| 5,391,144 | 2/1995 | Sakurai et al. | 606/169 |
| 5,808,396 | 9/1998 | Boukhny | 606/169 |
| 5,897,569 | 8/1999 | Kellogg et al. | 606/169 |

*Primary Examiner*—David J. Isabella
*Attorney, Agent, or Firm*—Poster, Lieder, Woodruff & Lucchesi

[57] ABSTRACT

A medical instrument (10) is used by a surgeon (S) operating on a patient (P). A surgical implement (12) is held by the surgeon performing the operation and is manipulable by him to bring a portion (14) of the implement into contact with the patient's body (B). A source (16) of ultrasonic pulses (18) produces a stream of such pulses which are supplied to the instrument. The method of the present invention enables pulses to be supplied to the instrument for a defined interval ($T_D$) after which there is a defined interval ($T_E$) in which no pulses are delivered. At the end of this pause pulses are again delivered to the instrument. Provision of a pause enable the surgeon to better control the operation, for example, by preventing overcutting of tissue.

7 Claims, 1 Drawing Sheet

USE OF PULSED ULTRASONICS IN SURGICAL APPLICATIONS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to the use of ultrasonic pulse phenomena in surgical processes, and more particularly, to the controlled use of ultrasonic pulses in performing a medical procedure such as an organ transplant.

The use of ultrasonics, including pulsed ultrasonics, is well-known in the surgical arts. In performing a surgical procedure, ultrasonic pulses are applied to a surgical instrument with the energy contained in the pulses being converted to a controlled movement of the instrument under the guidance and control of the operating surgeon. While efficacious in performing a variety of procedures, current techniques of supplying the pulses have a significant drawback. That is, the pulses are either continuously supplied to the instrument, or the supply is shut off. When the surgeon begins to use the instrument, he or she initiates the supply of pulses. This supply continues while the instrument is employed at the surgical site. When the surgeon removes the instrument from the site, the supply is stopped. However, heretofore, the surgeon has not been able to have a pause in the application of pulses which would allow him or her to keep the instrument in place while evaluating the progress of the surgery and what needs to be done next. Oftentimes, it is undesirable for the surgeon to have to remove the instrument, perform an evaluation, and then try to replace the instrument in its previous position before proceeding. The ability to have a built-in pause in the delivery of ultrasonic pulses, which would enable the surgeon to do an evaluation, while the instrument kept in place or near the surgical site, would be extremely useful in many surgeries.

BRIEF SUMMARY OF THE INVENTION

Among the several objects of the present invention may be noted the provision for control of the use of ultrasonic pulses with a surgical instrument in the performance of a surgical procedure so to provide a surgeon better control over an operation and provide better results for the patient;

the provision of such a control in which a stream of ultrasonic pulses applied to a surgical instrument operated by a surgeon is periodically interrupted for a predetermined interval and then automatically resumed after the interval;

the provision of such a control which enables a surgeon to evaluate the status of the procedure with the instrument being kept in place rather than having to be removed and then replaced;

the provision of such a control in which the interruption occurs at regular intervals and lasts for a specific period of time before the delivery of pulses resumes, or in which the surgeon controls both the occurrence and duration of each interruption;

the provision of such a surgical method including a programmable unit by which ultrasonic pulses are generated and delivered to the instrument and with which a surgeon or surgical team member programs the occurrence of each interuption in the delivery of pulses;

the provision of such a surgical method in which the surgeon remotely controls the unit to effect an interruption and the subsequent resumption in pulse delivery; and, the provision of such method to be useful in the performance of a variety of surgical procedures and to give the surgeon maximum flexibility in the use of a surgical instrument during a procedure.

In accordance with the invention, generally stated, a surgical instrument such as a knife, drill, burring tool or reamer used by a surgeon performing an operation is supplied ultrasonic pulses. A programmable unit generates a stream of such pulses which are supplied to the instrument. The supply of such pulses is periodically interrupted so the surgeon can evaluate the status of the procedure while the instrument is kept in place or immediately adjacent the surgical site. After a defined interval, the supply of pulses is resumed. The surgeon can also control the occurrence of an interruption and its duration for purposes of his or her evaluation. Other objects and features will be in part apparent and in part pointed out hereinafter.

BRIEF DESCRIPTION OF THE SEVERAL VIEWS OF THE DRAWINGS

In the drawings.

Corresponding reference characters indicate corresponding parts throughout the drawings.

DETAILED DESCRIPTION OF THE INVENTION

Figure 1:
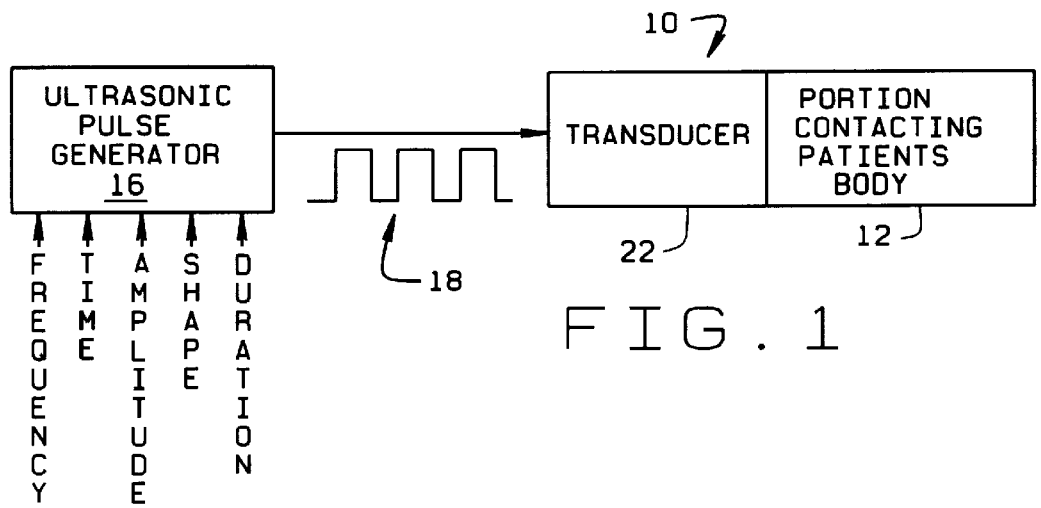
FIG. 1 is a simplified block diagram representing apparatus of the present invention for producing and supplying ultrasonic pulses to a surgical instrument.

Referring to the drawings, a surgeon S is shown in an operating theater T performing a surgical procedure on a patient P. In performing a surgical procedure, the surgeon uses a medical instrument indicated generally 10. The instrument is a surgical implement held by the surgeon, and manipulable by the surgeon to bring a portion 12 of the implement into contact with the patient's body B. A variety of surgical appliances are usable by the surgeon in this regard. These include surgical knives, drills, burring tools and reamers. The surgery being performed can be any of number of different surgeries including, for example, implantation of body organs.

Figure 2:
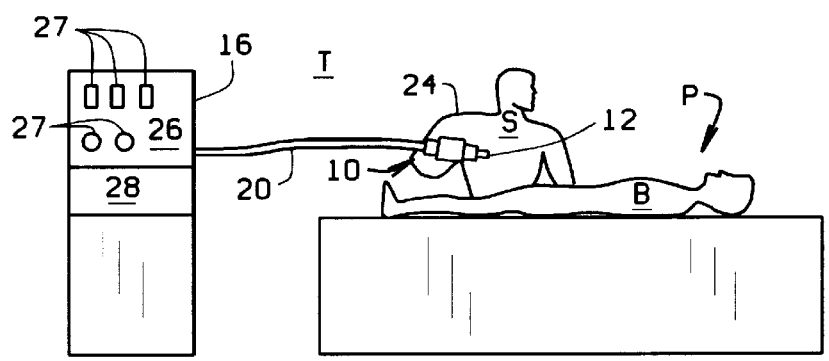
FIG. 2 illustrates an operating theater in which a surgeon employs an ultrasonically operated instrument of the present invention in operating on a patient; and, FIG. 3 is a time line illustrating delivery of ultrasonic pulse to a surgical instrument with a periodic interruption in the delivery of pulses for a defined interval.

A source 16 produces ultrasonic pulses 18 which are supplied to implement 10. Source 16 comprises an ultrasonic pulse generator which, as shown in FIG. 2, can be located within the operating room, or at any other convenient location. Ultrasonic pulses 18 produced by the generator are supplied to implement 10 via a conduit or cable 20. Within implement 10 is a transducer 22 to which the ultrasonic pulses are applied. The transducer, which is a movable portion 12 of the implement, or a separate element connected to the movable portion of the implement, converts the sonic energy transmitted by the ultrasonic pulses into physical movement by the movable portion of the implement. For example, movable portion 12 may comprise a surgical knife blade which is caused to move in certain manner in response to the converted energy. Or, the movable portion of the implement may be a rotary vibratory element such as is incorporated in a burring tool or reamer and whose degree of vibration or speed of rotation is a function of the converted ultrasonic energy. Those skilled in the art will appreciate that other surgical instruments using ultrasonic pulse energy may also be used in accordance with the teachings of the present invention.

Figure 3:
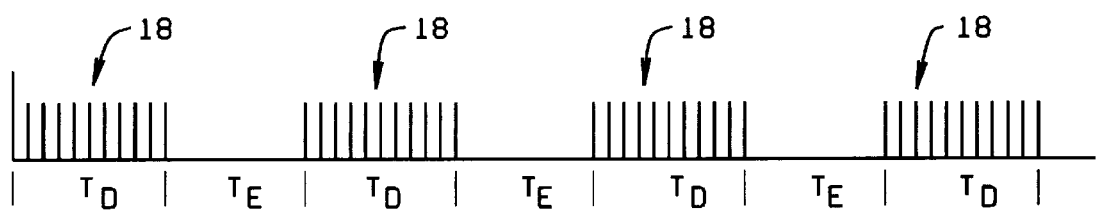

The pulse output of ultrasonic pulse generator 16 has controllable characteristics including the frequency at which pulses are generated, pulse amplitude and the shape and duration of individual pulses, and the spacing between pulses. Heretofore, when the flow of ultrasonic pulses is started, the flow of pulses to the instrument has been continuous until the surgeon stops the flow. During use of the instrument, a surgical knife, for example, one of the problems faced by the surgeon is overcutting of tissue. When the surgeon has made a desired cut, he wants to shut off the flow of pulses to the knife. Currently, if his reaction time is not fast enough some overcutting will occur. Further, in some instances, the surgeon will want to pause and inspect the surgical site, suction away blood or tissue, but do so without having to shut off the instrument, take it away from the site, and then move it back into place and restart the flow of pulses. In accordance with the teachings of the present invention, and as shown in FIG. 3, pulse generator 16 is now controllable to provide a stream of pulses for a defined interval $T_D$, automatically stop the flow of pulses for a defined interval $T_E$, and then automatically provide pulses for another defined interval $T_D$. This cycle of delivery, pause, delivery, pause, can last as long as the surgeon is using the instrument. By way of illustration, the time period $T_D$ of pulse delivery may be between 3–5 seconds, and the interval $T_E$ during which there is a pause in delivery, 3 seconds. By providing an automatic pause in the delivery of pulses, and by providing an interval of sufficient length in which no pulses are provided, the surgeon now knows that he can make a precise cut, for example, and then withdraw the blade when the pause occurs. He is therefore able to concentrate on the task at hand and not have to worry about stopping the cutting action because the cutting action is now automatically interrupted. For operations such as organ transplants where make precision cuts is of great concern, this allows the surgeon to better concentrate on making the correct cut and not worry about overcutting. This also yields better results for the patient.

It will be understood that besides having a predetermined interval $T_D$ in which pulses are delivered, and a predetermined interval $T_E$ in which there is a pause, both intervals may be variable and may be controlled by the surgeon. This is important because at different points in a procedure, the desired intervals may need be longer or shorter than at other periods. Pulse generator 16 is programmable to provide these varying intervals. Also, the intervals may differ depending upon the particular surgical instrument being used. Again, generator 16 can be programmed so that when one instrument is being used, one set of intervals $T_D$ and $T_E$ are.

What has been described is the use of ultrasonic pulses with surgical instruments in the performance of a surgical procedure. In accordance with the invention, a stream of controlled ultrasonic pulses are supplied to a surgical instrument. The length of time the pulses are supplied is automatically controlled. At the end of this interval, the pulses stop being supplied for a predetermined interval during which the surgeon can evaluate the status of the procedure. At the end of this pause, the supply of pulses automatically recommences. By not having to turn-on and turn-off the flow of pulses to the instrument, the surgeon is better able to concentrate on the procedure and provide a better result for the patient. An ultrasonic pulse generator can be preprogrammed prior to a surgery to supply the pulses and automatically pause, and the generator can be programmed for any of a series of different instruments used to perform different surgical procedures.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

What is claimed is:

1. A method of performing surgical operations in which a surgical instrument destroys the localized integrity of that to which the surgical instrument is in contact comprising:

generating series of ultrasonic pulses by an ultrasonic pulse generator, each series of ultrasonic pulses being generated for a predetermined period of time with a predetermined interval occurring between successive series of ultrasonic pulses, the ratio between the predetermined period for each series of pulses and the predetermined interval between successive series of pulses being at least 1:1;

supplying the ultrasonic pulses to a medical instrument operable by a surgeon performing an operation on a patient, the surgeon positioning a movable portion of the instrument adjacent an area of the patient's body on which the operation is performed;

destroying the localized integrity of that to which the surgical instrument is in contact by means of the surgical instrument; and, supplying each series of ultrasonic pulses to a transducer portion of the medical instrument which converts the energy contained in the pulses and supplies the energy to the movable portion of the instrument to move the movable portion of the instrument and perform the operation on the patient, movement of the movable portion of the instrument for the predetermined period of time with the predetermined interval between movements allowing the surgeon to evaluate the status of the operation as it progresses.

2. The method of claim 1 wherein the medical instrument is one of a surgical knife, drill, burring tool, or reamer.

3. The method of claim 1 in which the frequency, amplitude, shape, and duration of each pulse, and the interval between each pulse in a series of pulses is controllable.

4. The method of claim 1 which the ratio ranges between 1:1 to approximately 1.67:1.

5. The method of claim 4 in which the duration of each series of pulses is 3–5 seconds.

6. The method claim 5 in which the predetermined interval between each series of pulses is approximately 3 seconds.

7. The method of claim 1 for use in organ transplantation.

* * * * *